United States Patent
Kogan

(10) Patent No.: US 6,444,993 B1
(45) Date of Patent: Sep. 3, 2002

(54) APPARATUS FOR RADIATION ANALYSIS WITH A VARIABLE COLLIMATOR

(75) Inventor: Vladimir Kogan, Almelo (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/621,524

(22) Filed: Jul. 21, 2000

(30) Foreign Application Priority Data

Jul. 23, 1999 (EP) .............................................. 99202443

(51) Int. Cl.[7] ................................................. G21K 1/00
(52) U.S. Cl. ...................... 250/505.1; 378/149; 378/150
(58) Field of Search ....................... 250/505.1; 378/152, 378/147, 149, 150, 145

(56) References Cited

U.S. PATENT DOCUMENTS

| | | | | |
|---|---|---|---|---|
| 4,127,398 A | * | 11/1978 | Singer, Jr. ...................... | 65/4 A |
| 4,205,228 A | * | 5/1980 | Tosswill ...................... | 250/336 |
| 5,165,106 A | * | 11/1992 | Barthelmes et al. ...... | 250/505.1 |
| 5,192,869 A | * | 3/1993 | Kumakhov ............... | 250/505.1 |

OTHER PUBLICATIONS

Patent Abstracts of Japan, Application No. 08208931, Publication No. 10038823.

* cited by examiner

Primary Examiner—Kiet T. Nguyen

(57) ABSTRACT

In apparatus for radiation analysis, for example, X-ray spectrometers, the aperture angle of the analysing radiation beam 45 is often desired to vary during the measuring process. The aperture angle of the radiation beam is determined, for example, by the length of the collimating elements 46, 60 in the collimator. In accordance with the invention, this is achieved by displacing or rotating the collimator through the radiation beam 45, so that the collimating element length L exposed to the radiation beam can be varied in consequence. A collimator comprising rectangular plates 46 (Soller collimator) can be rotated around a shaft 50 perpendicular to the plates, or a collimator comprising X-ray fibres 60 can be arranged with varying fibre lengths and displace them through the radiation beam transversely to the longitudinal direction of the fibres.

12 Claims, 3 Drawing Sheets

APPARATUS FOR RADIATION ANALYSIS WITH A VARIABLE COLLIMATOR

BACKGROUND OF THE INVENTION

1. Field of the Invention

The invention relates to an apparatus for radiation analysis of a sample to be examined, in which a radiation beam runs along an optical path from a radiation source to a radiation detector via the sample to be examined, in which optical path a collimator with collimating elements is present, which collimator, as a result of a movement through the radiation beam, exhibits a variable aperture angle for the radiation beam.

The invention likewise relates to a collimator to be used in such an apparatus.

2. Description of the Related Art

Such apparatus is known from "Patent Abstracts of Japan", Application number 08208931, Publication number 10038823 A. In said document, the apparatus for radiation analysis is formed by a spectrometer for X-ray fluorescence. In the X-ray optical path of this known spectrometer, there are two collimators in the form of so-called Soller-slit collimators. Such collimators comprise a stack of mutually parallel plates of an X-ray-absorbing material which show certain spacings. A collimating element in such a collimator is thus formed by a spacing plus the adjacent plates. The aperture angle exhibited to the radiation beam by such an assembly of plates is equal to twice the ratio of the spacing to the length of the plates in the place of the X-ray beam passing the plates.

Apparatus for radiation analysis are often arranged for measuring a high-resolution spectrogram (for example, X-ray spectrometers) or diffraction pattern (for example, X-ray diffractometers). For certain rays in the radiation beam there are then deviations from the ideal radiation path, which have an adverse effect on the resolution of the measurements. To mitigate these deviations, it is known per se to install a collimator for bounding the radiation beam, more particularly bounding the aperture angle of the radiation beam, in the optical path of the apparatus.

A measurement with an X-ray spectrometer or an X-ray diffractometer often comprises making an angular scan, that is to say, the radiation intensity coming from the sample to be examined is measured for a large range of angular values around the sample. Said deviations from the ideal radiation path are then dependent on the angular value. To keep the measuring time with these apparatus shortest possible, the aperture angle (thus the total intensity) of the radiation beam is desirably not further confined than is necessary for the resolution. Therefore, during the measurement the aperture angle of the collimator is desirably made variable, that is, depending on the angular value.

In the X-ray spectrometer known from said document, this variable value of the aperture angle is achieved by arranging the Soller slit collimators shown there and comprising a stack of plates with equal mutual spacings, in such a way that the stack of plates comprises a plurality of sub-stacks exhibiting mutually different spacings between the plates. A different aperture angle may now be selected by displacing the respective Soller-slit collimator in a direction perpendicular to the surface of the plate, so that another sub-stack is inserted into the radiation beam.

Manufacturing a collimator in which the collimating elements have mutually different dimensions is inconvenient from the point of view of manufacturing. Besides, only some discrete values of the aperture angle can be realised in this known manner, or (with a continuously varying spacing) there are a plurality of spacings in the beam at the same time, so that the aperture angle is not defined well.

SUMMARY OF THE INVENTION

It is an object of the invention to provide an apparatus for radiation analysis in which the aperture angle of the radiation beam is continuously variable and which can be manufactured in a relatively simple manner. For this purpose, the apparatus according to the invention is characterised in that the collimator can be moved through the radiation beam in such a way that the collimating element length exposed to the radiation beam allows of variation as a result. The invention is based on the recognition that the intended variation of the aperture angle can be obtained by a movement so that the dimensional differences, as they are often inherent in all sorts of equipment, are the cause of this variation in the aperture angle. However, it is not necessary for these inherent dimensional differences to be utilised; it is alternatively possible to apply dimensional differences that are easy to manufacture.

In an embodiment of the invention, in which inherent dimensional differences are utilised in a simple manner, the collimating elements have the form of mutually parallel plates, and said movement comprises a rotation around a shaft perpendicular to the plates. As a result of said rotation, the radiation beam will generally follow another path relative to the collimator, so that the beam encounters different dimensions.

In a further embodiment of the invention, in which inherent dimensional differences are utilised in a simple manner, the plates have a rectangular shape. This provides a high degree of simplicity in the manufacturing process with a shape that has already been of general use in this technique.

In another embodiment of the invention, the plates have, at least partly, an elliptical shape. In a strongly divergent radiation beam this measure makes it possible to reduce the difference in aperture angle for different trajectories in the beam.

In yet another embodiment of the invention, the collimating elements have the form of channels having a cross section closed in itself, which channels have mutually different lengths, and said movement comprises a displacement transverse to the longitudinal direction of the channels. The channels may be embodied as X-ray optical fibres, f.i. glass fibres. X-ray optical fibres are known per se for influencing the ray path in a radiation beam. Such fibres, however, are very thin, so that a collimator made of fibres comprises a very large number of fibres and cannot easily be manufactured in an arbitrary shape. However, it is highly possible indeed to make a stack of fibres so that this stack in side-elevation has the form of, for example, a triangle; by displacing the thus formed collimator transversely to the longitudinal axis of the fibbers, fibres of ever different lengths are fed into the beam.

BRIEF DESCRIPTION OF THE DRAWINGS

The invention will be described in more detail with reference to the drawing Figures in which like reference numerals denote like elements. Therein.

DETAILED DESCRIPTION OF THE PREFERRED EMBODIMENTS

The invention will be described with reference to an embodiment in which the apparatus for radiation analysis is formed by an X-ray analysis apparatus, more particularly, an X-ray diffraction apparatus. Therein, the analysing radiation has the form of X-ray radiation. However, there should be pointed out that the invention is applicable to all further apparatus for radiation analysis in which a collimator is used for the analysing radiation beam.

Figure 1:
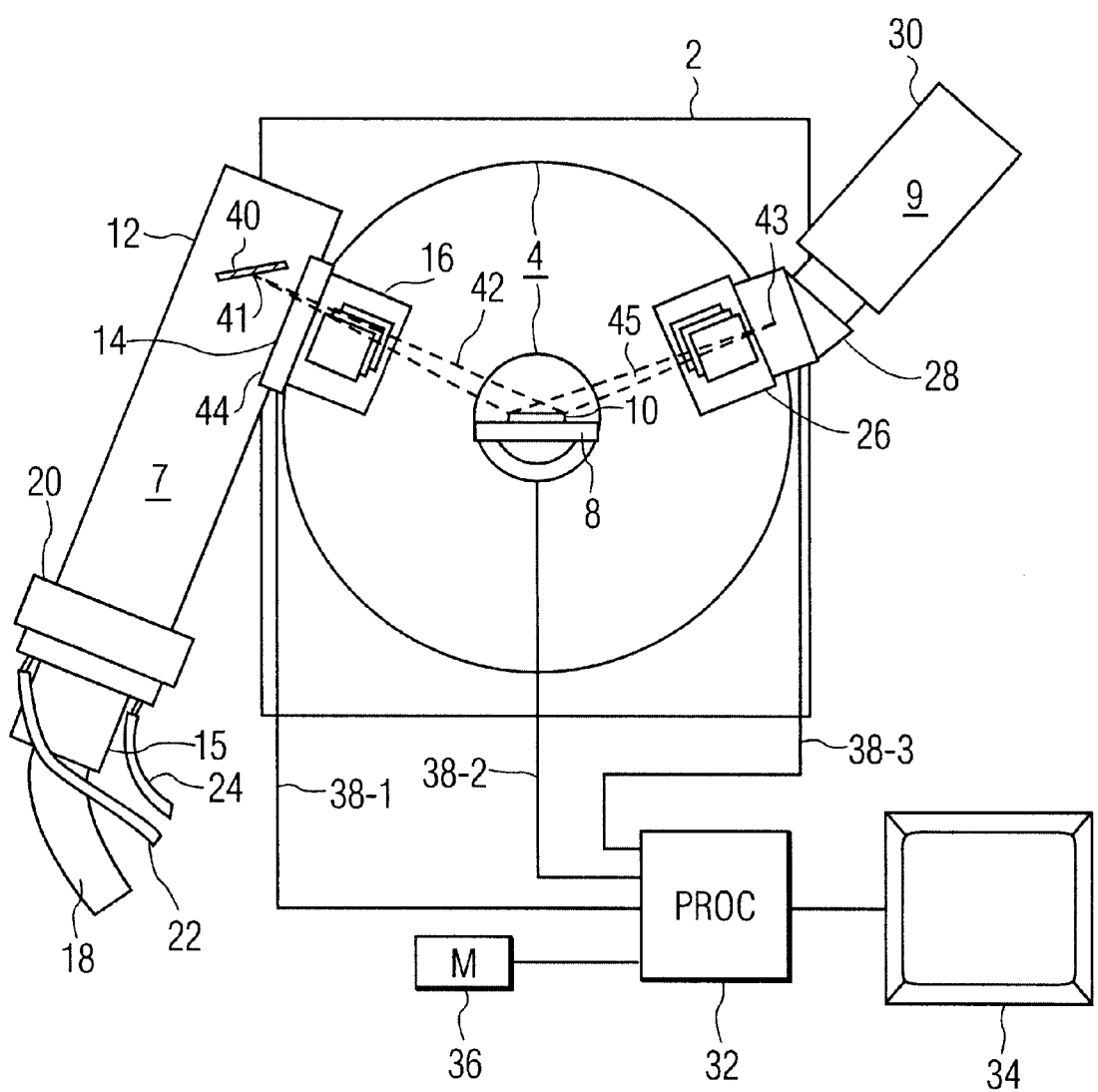
FIG. 1 gives a global representation of an X-ray analysis apparatus known per se in which the invention may be applied.

FIG. 1 is a diagrammatic representation of a known X-ray analysis apparatus, in this case being an X-ray diffraction apparatus. In this apparatus a goniometer 4 is mounted on a frame 2. This goniometer 4 can be provided with an angular encoder for measuring the angular rotation of the X-ray source 7 which is mounted thereon and of the detector device 9 which is also mounted thereon. The goniometer is furthermore provided with a sample holder 8 on which a sample 10 is arranged. An angular encoder may be provided on the sample holder for the cases where measurement of the angular rotation of the sample is important. The X-ray source 7 includes a holder 12 for an X-ray tube (not shown in the Figure) which is secured in the holder by way of a fixing ring 20. This X-ray tube includes a high-voltage connector 15 for applying the high voltage and the filament current to the X-ray tube via high-voltage cable 18. On the same side of the X-ray tube, supply and discharge ducts 22 and 24 for the cooling water of the X-ray tube are provided. The tube holder 12 further includes an exit window for X-rays 44 and a unit 16 for parallelization of the X-ray beam (a Soller-slit collimator). The plates of the Soller-slit collimator 16 are parallel to the plane of drawing in such a way that the X-ray beam generated by the X-ray source 7 illuminates the sample 10 with a divergent beam. The detector device 9 comprises a holder 26 for a Soller-slit collimator, a holder 28 for a monochromator crystal, and a detector 30. The plates of the Soller-slit collimator in holder 26 are also parallel to the plane of drawing. If the X-ray source and the detector are both rotatable around the sample, it is not necessary for the sample to be mounted so as to be rotatable. However, it is alternatively possible to mount the X-ray source so as to be stationary as this may sometimes be necessary in the case of voluminous and heavy X-ray sources. In that case, the sample holder as well as the detector should be rotatable.

The X-ray diffraction apparatus as shown in FIG. 1 also includes a processing device for processing the various measured data. This processing device comprises a central processing unit 32 with a memory unit 36 and a monitor 34 for the presentation of the various data and for the display of the measured and calculated result. The X-ray source 7, the detector device 9 and the sample holder 8, mounted on the goniometer 4, are all provided with a unit (not shown) for determining the angular position of the respective element relative to the scaled graduation of the goniometer. A signal representing this angular position is transferred to the central processing unit 32 via connection leads 38-1, 38-2 and 38-3.

FIG. 1 shows a so-called Bragg-Brentano arrangement, which means that the X-rays emanating from a single point are again focused at one point after reflection by the sample 10, provided that the surface of the sample is tangent to a circle through the point of origin and the focal point. The sample 10 is irradiated by means of X-rays originating from the X-ray source 7. An anode 40, which forms part of the X-ray tube that is not further shown in this Figure, is diagrammatically represented in this X-ray source. In anode 40 the X-rays are generated in a customary manner by exposing this anode to high-energetic electrons. As a result, X-rays 42 emanating from X-ray window 44 are generated in the anode. The said point of origin in the arrangement shown in FIG. 1 is not formed by a single point, but by a line focus 41 on the anode which line focus is perpendicular to the plane of drawing. Said focal point is formed by the point of union 43 of the beam 45 leaving the sample at the area of the entrance of the detector 30. Consequently, this arrangement has a focusing effect only in the plane of drawing.

Figure 2A:
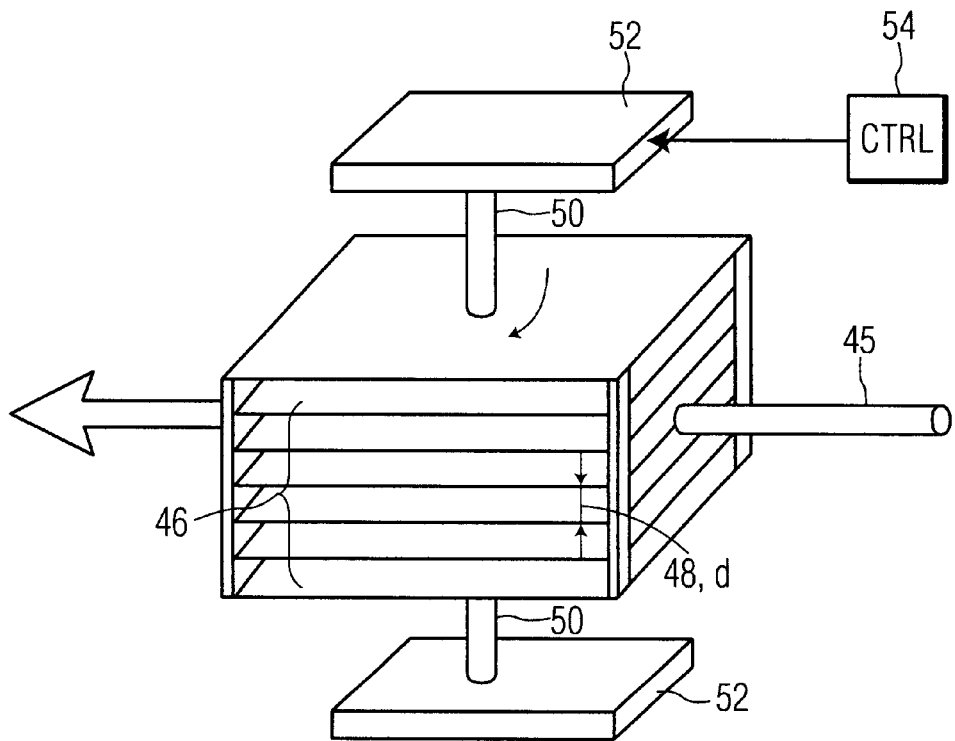
FIG. 2a shows a perspective view of a first embodiment of a variable Soller-slit collimator according to the invention.
Figure 2B:
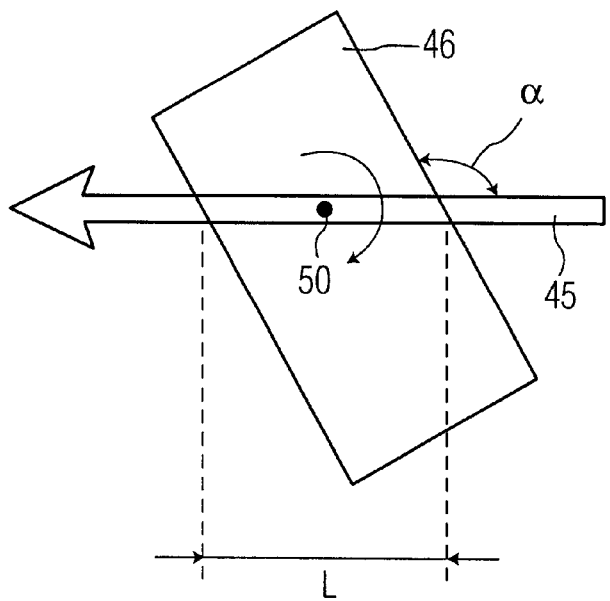
FIG. 2b shows a top view of a collimator plate of the collimator as shown in FIG. 2a, together with the radiation beam.

FIG. 2 shows a respective view of an embodiment of a variable Soller-slit collimator in which the plates of the collimator have a rectangular shape. The collimator shown comprises a stack of collimator plates 46 with spacings 48. All the plates in this collimator have the same dimensions. A radiation beam 45 whose aperture angle is bounded by the collimator is incident in parallel with the plane of the collimator plates 46. The angle of aperture $\alpha$ of the radiation beam is given by twice the ratio of spacing d between the plates 46 to the collimating element length L exposed to the radiation beam (see also FIG. 2b), so that the following holds $\alpha=2d/L$.

The value of the magnitude L may be varied by rotating the collimator plates around a shaft 50 that is perpendicular to the plane of the plates 46. For this purpose, a movement mechanism is provided, in this embodiment formed by a shaft 50 and a drive unit 52 in which the shaft 50 is carried in bearings and which is fixedly connected to the analysis apparatus the collimator forms part of. The drive unit comprises, for example, a motor for rotating the shaft, which motor is controlled by a control unit 54 which may form part of a computer belonging to the analysis apparatus.

When the measurements to be carried out by the analysis apparatus so require, the collimator plates 46 are rotated around the shaft 50 until the correct aperture angle is reached, that is, until the relationship $\alpha=2d/L$, where $\alpha$ is a prescribed value, has been satisfied.

Figure 3:
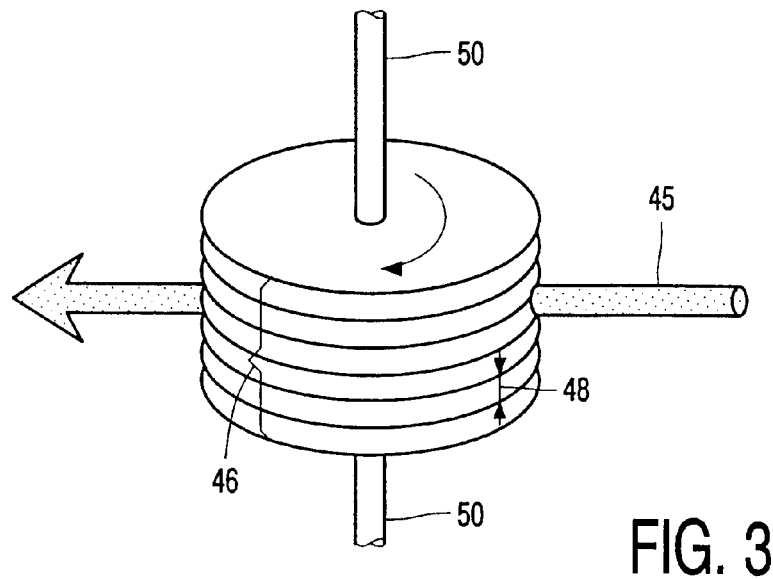
FIG. 3 shows a perspective view of a second embodiment of a variable Soller slit collimator according to the invention.

FIG. 3 shows a perspective view of a second embodiment of a variable Soller-slit collimator according to the invention. This embodiment is pre-eminently suitable for the devices in which the radiation beam is strongly diverging or converging in a plane parallel to the collimator plates. This situation may occur, for example, in a spectrometer of the Bragg-Brentano type. With a beam so divergent, the value of L (i.e. the collimator plate length L exposed to the radiation beam 45) is not the same for all the rays in the radiation beam. This may be a disadvantage for measurements that require a high degree of accuracy. It can be demonstrated that for such measurements a Soller-slit collimator having elliptically shaped plates eliminates this disadvantage entirely or to a large extent. Just like in the collimator as shown in FIG. 2, the collimator in FIG. 3 is driven via shaft 50 in the same way as has already been described with reference to FIG. 2.

Figure 4:
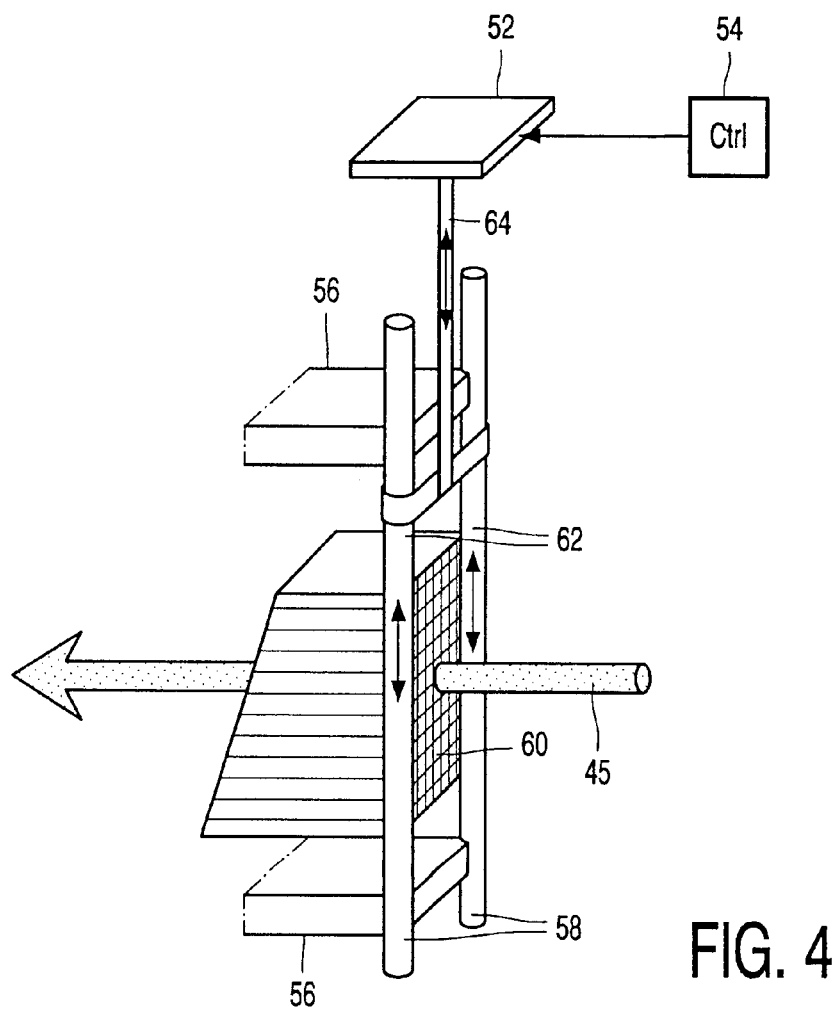
FIG. 4 shows a perspective view of an embodiment of a variable Soller-slit collimator with X-ray optical fibres according to the invention.

FIG. 4 shows a perspective view of an embodiment of a variable Soller-slit collimator with X-ray optical fibres according to the invention. Such fibres are known per se for influencing radiation beams of X-rays. With such fibres, a high degree of collimation, i.e. a very small aperture angle of the radiation beam, may be obtained.

The collimator shown in this Figure comprises a two-dimensional stack of X-ray fibres 60. The X-ray fibres 60 have the same cross-section, but a length that depends on their height in the stack. Parallel with the axial direction of the X-ray fibres 60, a radiation beam 45 is incident whose aperture angle is bounded by the stack of X-ray fibres. The aperture angle of the radiation beam is determined by the ratio of the internal cross section and the length of the hollow fibre. The aperture angle may thus be varied by reciprocating the collimator. For this purpose, a movement mechanism is provided in this embodiment, which is formed by a holder for the stacking of X-ray fibres, which holder comprises two guides 62 which may be reciprocated by a driving rod 64, the guides 62 being led along parts 56 of the arrangement of the analysis apparatus. The driving of said movement is performed by a drive unit 52 in which the driving rod 64 is carried in bearings and which is also fixedly connected to the analysis apparatus. The drive unit comprises, for example, a motor for reciprocating the driving rod, which motor is controlled by a control unit 54 which may form part of a computer belonging to the analysis apparatus. When the measurements to be performed by the analysis apparatus so require, the collimator is reciprocated until the correct aperture angle is reached.

What is claimed is:

1. An apparatus for radiation analysis of a sample to be examined, in which a radiation beam runs along an optical path from a radiation source to a radiation detector via the sample to be examined, in which optical path a collimator with collimating elements is present, said collimator, as a result of a movement through the radiation beam, exhibits a variable aperture angle for the radiation beam, wherein the collimating elements are rotated through the radiation beam to vary a magnitude of a collimating element length (L) exposed to the radiation beam.

2. An apparatus for radiation analysis as claimed in claim 1, in which the collimating elements have the form of mutually parallel plates and in which said movement comprises a rotation around a shaft perpendicular to the plates.

3. An apparatus for radiation analysis as claimed in claim 2, in which the plates have an elliptical shape.

4. An apparatus for radiation analysis as claimed in claim 2, in which the plates at least partly have an elliptical shape.

5. An apparatus for radiation analysis as claimed in claim 1, in which collimating elements have the form of channels, said channels having a same-size cross section and mutually different lengths, and said movement of the collimating elements comprises a displacement transverse to the longitudinal direction of the channels.

6. An apparatus for radiation analysis as claimed in claim 5, in which the channels are embodied as X-ray optical fibers.

7. A collimator to be used in an apparatus for radiation analysis by means of a radiation beam, with a plurality of collimating elements arranged with spacing between each of the collimating elements, said collimator comprising a movement mechanism for movement of the collimating elements through the radiation beam, so that the collimator exhibits a variable aperture angle for the radiation beam along a longitudinal direction of the collimating elements, wherein the movement mechanism is arranged for exposing a variable length (L) of the collimating elements to the radiation beam so that, as a result, the variable aperture angle for the radiation beam is obtained.

8. A collimator as claimed in claim 7, in which the collimating elements have the shape of mutually parallel plates, and in which the movement mechanism is arranged for rotating the collimator around a shaft perpendicular to the plates.

9. A collimator as claimed in claim 8, in which the plates have a rectangular shape.

10. A collimator as claimed in claim 8, in which the plates at least partly have an elliptical shape.

11. A collimator as claimed in claim 7, in which the collimating elements are in the form of channels having a cross section in itself in which channels have mutually different lengths, and in which the movement mechanism is arranged for displacing the collimator transversely to the longitudinal direction of the channels.

12. A collimator as claimed in claim 11, in which the channels are embodied as X-ray optical fibers.

* * * * *